US 7,715,898 B2

(12) United States Patent
Anderson

(10) Patent No.: US 7,715,898 B2
(45) Date of Patent: May 11, 2010

(54) SYSTEM AND METHOD FOR EMPLOYING MULTIPLE COIL ARCHITECTURES SIMULTANEOUSLY IN ONE ELECTROMAGNETIC TRACKING SYSTEM

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 718 days.

(21) Appl. No.: 11/289,849

(22) Filed: Nov. 30, 2005

(65) Prior Publication Data
US 2006/0106292 A1 May 18, 2006

Related U.S. Application Data

(63) Continuation-in-part of application No. 10/670,054, filed on Sep. 24, 2003.

(51) Int. Cl.
*A61B 5/05* (2006.01)
(52) U.S. Cl. .................. 600/407; 600/410; 600/409; 324/207; 324/258
(58) Field of Classification Search .......... 600/407, 600/409, 410, 422, 301; 335/299; 324/207, 324/258; 336/199
See application file for complete search history.

(56) References Cited

U.S. PATENT DOCUMENTS

| 3,868,565 | A | 2/1975 | Kuipers |
| 3,983,474 | A | 9/1976 | Kuipers |
| 4,054,881 | A | 10/1977 | Raab |
| 4,176,662 | A | 12/1979 | Frazer |
| 4,613,866 | A | 9/1986 | Blood |
| 4,618,822 | A | 10/1986 | Hansen |
| 4,622,644 | A | 11/1986 | Hansen |
| 4,642,786 | A | 2/1987 | Hansen |
| 4,710,708 | A | 12/1987 | Rorden et al. |
| 4,737,794 | A | 4/1988 | Jones |
| 4,742,356 | A | 5/1988 | Kuipers |
| 5,099,845 | A | 3/1992 | Besz et al. |

(Continued)

FOREIGN PATENT DOCUMENTS

EP 0543551 A1 * 5/1993

(Continued)

OTHER PUBLICATIONS

Peter T. Anderson, A Source of Accurately Calculable Quasi-Static Magnetic Fields, Oct. 2001.

(Continued)

*Primary Examiner*—Long V Le
*Assistant Examiner*—Joel F Brutus
(74) *Attorney, Agent, or Firm*—McAndrews, Held & Malloy, Ltd.; Peter J. Vogel; Michael A. Dellapenna

(57) ABSTRACT

The presently described technology provides a method for simultaneously employing two or more coil architectures in an electromagnetic tracking system. The method includes providing a transmitter that includes three single-coil transmitters, one or more receivers each including three single-coil receivers, and a receiver array that includes a plurality of single-coil receivers; tracking one or more of the single-coil transmitters of the transmitter with respect to the receiver array; and simultaneously tracking one or more of the receivers with respect to the transmitter.

19 Claims, 3 Drawing Sheets

U.S. PATENT DOCUMENTS

| | | | |
|---|---|---|---|
| 5,211,165 A | 5/1993 | Dumoulin et al. | |
| 5,251,635 A | 10/1993 | Dumoulin et al. | |
| 5,255,680 A | 10/1993 | Darrow | |
| 5,265,610 A | 11/1993 | Darrow | |
| 5,307,072 A | 4/1994 | Jones | |
| 5,377,678 A * | 1/1995 | Dumoulin et al. | 600/424 |
| 5,425,367 A | 6/1995 | Shapiro | |
| 5,425,382 A | 6/1995 | Golden et al. | |
| 5,437,277 A | 8/1995 | Dumoulin | |
| 5,443,066 A | 8/1995 | Dumoulin et al. | |
| 5,445,150 A | 8/1995 | Dumoulin et al. | |
| 5,517,195 A | 5/1996 | Narlow et al. | |
| 5,558,091 A | 9/1996 | Acker et al. | |
| 5,570,021 A | 10/1996 | Dachniwskyj | |
| 5,592,939 A | 1/1997 | Martinelli | |
| 5,622,169 A | 4/1997 | Golden et al. | |
| 5,676,673 A | 10/1997 | Ferre et al. | |
| 5,747,996 A * | 5/1998 | Fuchs | 324/207.17 |
| 5,803,089 A | 9/1998 | Ferre et al. | |
| 5,829,444 A | 11/1998 | Ferre et al. | |
| 5,873,822 A | 2/1999 | Ferre et al. | |
| 5,876,325 A * | 3/1999 | Mizuno et al. | 600/102 |
| 5,967,980 A | 10/1999 | Ferre et al. | |
| 6,039,701 A * | 3/2000 | Sliwa et al. | 600/588 |
| 6,052,610 A | 4/2000 | Koch | |
| 6,073,043 A | 6/2000 | Schneider | |
| 6,129,667 A | 10/2000 | Dumoulin | |
| 6,129,668 A | 10/2000 | Haynor et al. | |
| 6,175,756 B1 | 1/2001 | Ferre et al. | |
| 6,177,792 B1 | 1/2001 | Govari | |
| 6,188,355 B1 | 2/2001 | Gilboa | |
| 6,201,987 B1 | 3/2001 | Dumoulin | |
| 6,226,547 B1 | 5/2001 | Lockhart | |
| 6,230,038 B1 | 5/2001 | von Gutfeld et al. | |
| 6,233,476 B1 | 5/2001 | Strommer et al. | |
| 6,246,898 B1 | 6/2001 | Vesely et al. | |
| 6,259,372 B1 | 7/2001 | Taranowski et al. | |
| 6,289,233 B1 * | 9/2001 | Dumoulin et al. | 600/410 |
| 6,341,231 B1 | 1/2002 | Ferre et al. | |
| 6,369,564 B1 | 4/2002 | Khalfin et al. | |
| 6,374,131 B1 | 4/2002 | Tomita et al. | |
| 6,374,134 B1 | 4/2002 | Bladen | |
| 6,427,079 B1 | 7/2002 | Schneider et al. | |
| 6,445,943 B1 | 9/2002 | Ferre et al. | |
| 6,456,074 B1 | 9/2002 | Minas | |
| 6,459,882 B1 | 10/2002 | Palermo | |
| 6,463,039 B1 | 10/2002 | Ricci | |
| 6,472,975 B1 | 10/2002 | Beigel et al. | |
| 6,490,475 B1 | 12/2002 | Seeley et al. | |
| 6,492,816 B1 | 12/2002 | Feenan | |
| 6,636,757 B1 | 10/2003 | Jascob et al. | |
| 6,774,624 B2 | 8/2004 | Anderson et al. | |
| 6,856,826 B2 | 2/2005 | Seeley et al. | |
| 6,856,827 B2 | 2/2005 | Seeley et al. | |
| 2002/0008516 A1 | 1/2002 | Dietz | |
| 2005/0003757 A1 | 1/2005 | Anderson | |
| 2005/0012597 A1 | 1/2005 | Anderson | |

FOREIGN PATENT DOCUMENTS

| | | |
|---|---|---|
| EP | 1193507 | 3/2002 |
| JP | 01303140 | 12/1989 |
| JP | 09000507 | 1/1997 |

OTHER PUBLICATIONS

Tom Ahlkvist Scharfeld, An Analysis of the Fundamental Constraints on Low Cost Passive Radio-Frequency Identification System Design, Aug. 2001.

* cited by examiner

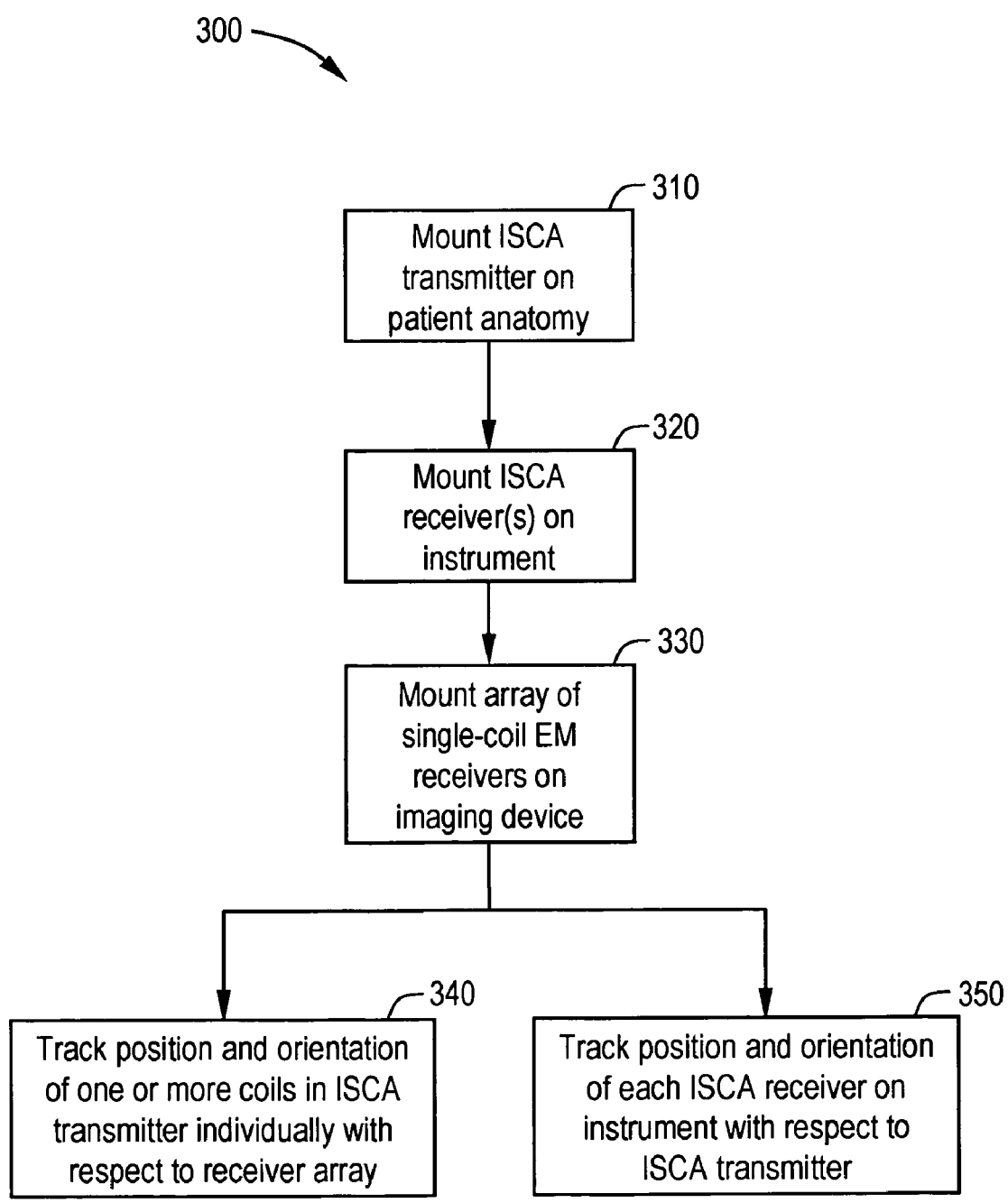

SYSTEM AND METHOD FOR EMPLOYING MULTIPLE COIL ARCHITECTURES SIMULTANEOUSLY IN ONE ELECTROMAGNETIC TRACKING SYSTEM

RELATED APPLICATIONS

The present application is a continuation-in-part of U.S. patent application Ser. No. 10/670,054 (the "'054 application"), U.S. Patent Application Publication No. US-2005-0065433-A1, entitled "System and Method for Software Configurable Electromagnetic Tracking," which names Peter Traneus Anderson as inventor and was filed on Sep. 24, 2003. The '054 application is hereby incorporated by reference herein in its entirety.

FEDERALLY SPONSORED RESEARCH OR DEVELOPMENT

Not Applicable.

BACKGROUND OF THE INVENTION

The present invention generally relates to an electromagnetic tracking system. In particular, the present invention relates to a system and method for the use of multiple coil architectures simultaneously in one electromagnetic ("EM") tracking system.

Medical practitioners, such as doctors, surgeons, and other medical professionals, often rely upon technology when performing a medical procedure, such as image-guided surgery ("IGS") or examination. An IGS system can provide positioning and/or orientation ("P&O") information for the medical instrument with respect to the patient or a reference coordinate system, for example. A medical practitioner can refer to the IGS system to ascertain the P&O of the medical instrument when the instrument is not within the practitioner's line of sight with regard to the patient's anatomy, or with respect to non-visual information relative to the patient. An IGS system can also aid in pre-surgical planning.

The IGS or navigation system allows the medical practitioner to visualize the patient's anatomy and track the P&O of the instrument. The medical practitioner can use the tracking system to determine when the instrument is positioned in a desired location or oriented in a particular direction. The medical practitioner can locate and operate on, or provide therapy to, a desired or injured area while avoiding other structures. Increased precision in locating medical instruments within a patient can provide for a less invasive medical procedure by facilitating improved control over smaller, flexible instruments having less impact on the patient. Improved control and precision with smaller, more refined instruments can also reduce risks associated with more invasive procedures such as open surgery.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images can be taken to display, correct the P&O of, or otherwise navigate a tool or instrument involved in the procedure.

Generally, image-guided surgery systems operate with an image display which is positioned in a surgeon's field of view and which displays a few panels such as a selected MRI image and several x-ray or fluoroscopic views taken from different angles. In tool navigation systems, the display visible to the surgeon may show an image of a surgical tool, biopsy instrument, pedicle screw, probe or other device projected onto a fluoroscopic image, so that the surgeon can visualize the orientation of the surgical instrument in relation to the imaged patient anatomy. An appropriate reconstructed CT or MRI image, which may correspond to the tracked coordinates of the probe tip, can also be displayed.

Among the systems that have been proposed for effecting such displays, many rely on closely tracking the position and orientation of the surgical instrument in external coordinates. The various sets of coordinates can be defined by robotic mechanical links and encoders, or more usually, are defined by a fixed patient support, two or more receivers such as video cameras which can be fixed to the support, and a plurality of signaling elements attached to a guide or frame on the surgical instrument that enable the position and orientation of the tool with respect to the patient support and camera frame to be automatically determined by triangulation, so that various transformations between respective coordinates can be computed.

The highly accurate tracking technology found in navigation systems can also be used to track the P&O of items other than medical instruments in a variety of applications. That is, a tracking system can be used in other settings where the P&O of an object in an environment is difficult to accurately determine by direct or indirect inspection. For example, tracking technology can be used in forensic or security applications. Retail stores can use tracking technology to prevent theft of merchandise. In such cases, a passive transponder can be located on the merchandise. A transmitter can be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems can be used to monitor the position of a person in a simulated environment. A transponder or transponders can be located on a person or object. A transmitter emits an excitation signal and a transponder produces a response signal. A receiver detects the response signal. The signal emitted by the transponder can then be used to monitor the position of a person or object in a simulated environment.

Tracking systems can be optical, ultrasonic, inertial, or electromagnetic, for example. Electromagnetic tracking systems can employ coils as receivers and transmitters. In EM trackers, transmitter coil or coils emit quasi-static magnetic fields. In addition, receiver coil(s) measure these fields. From the field measurements and mathematical models of the coils, the position and orientation of the receiver with respect to the transmitter can be determined. Alternatively, the position and orientation of the transmitter with respect to the receiver is determined.

Typically, an electromagnetic tracking system is configured in an industry-standard coil architecture ("ISCA"). ISCA trackers use a trio of nearly-colocated, nearly-orthogonal, nearly-dipole coils for the transmitter and another trio of nearly-colocated, nearly-orthogonal, nearly-dipole coils for the receiver. Each coil trio is carefully characterized during manufacture to numerically express the precise value of the "nearly" in the previous sentence. From the field measurements and mathematical models of the coils, the position and orientation of the receiver with respect to the transmitter is determined. Alternatively, the position and orientation of the transmitter with respect to the receiver is determined. All six degrees of freedom (three of position and three of orientation) are tracked.

Single-coil EM trackers use a single dipole or nearly-dipole transmitter coil and an array of six or more receiver coils, or else use a single dipole or nearly-dipole receiver coil and an array of six or more transmitter coils. By electromagnetic reciprocity, these two arrangements function equivalently. The coils in the array can be dipole, nearly-dipole, or non-dipole coils (or combinations). The coils in the array are either precisely manufactured or precisely characterized during manufacture to obtain mathematical models of the coils in the array. The single coil does not need to be characterized. From the field measurements and mathematical models, the position and orientation of the single coil with respect to the array are tracked. Since the single coil is symmetrical about its roll axis, only five degrees of freedom (six of position and two of orientation) of position and orientation are tracked. The gain of the single coil can also be tracked.

The array of coils can be fabricated as a printed-circuit board or as an array of wound coils or as a combination of both. Arrangements of coils in the array vary widely in various implementations of single-coil EM trackers. The array can include electrically-conductive or ferromagnetic materials as part of the design of the array.

The big disadvantage of single-coil EM trackers is the need to find a place to put the array of coils. To work well, this array needs to be physically spread out in space.

Note that a multichannel single-coil EM tracker can track two or three single coils simultaneously. If two or more single coils are mounted rigidly with respect to each other with their axes pointed in different directions, and tracked as two or more single coils or as a group, all six degrees of freedom could be tracked for the set of single coils.

In current systems and methods employing a fluoroscope, an ISCA transmitter is rigidly mounted on the relevant anatomy of a patient to serve as a dynamic reference. One or two ISCA receivers are mounted on the x-ray image detector of a fluoroscope. The ISCA receivers are spaced away from the surface of the detector, to reduce the effects of field distortion.

When taking a fluoroscopic image, the detector can be tracked with respect to the ISCA transmitter in order to determine the position and orientation of the image intensifier with respect to the relevant anatomy of the patient.

One or two ISCA receivers are also mounted on a surgical instrument being navigated. The instrument ISCA receivers can then be tracked with respect to the ISCA transmitter in order to determine the position and orientation of the surgical instrument with respect to the relevant anatomy of the patient. The real-time position and orientation of the surgical instrument is then calculated and displayed on stored fluoroscopic images.

One major difficulty with current systems and methods is that the electrically-conductive materials and ferromagnetic materials in the fluoroscope detector distort the magnetic fields near the ISCA receivers mounted on the detector. ISCA EM trackers are very sensitive to such field distortion, leading to inaccurate tracking or failure to track at all in severe cases. However, in general, the detector can be far enough from the instrument that the detector does not significantly distort the fields at the ISCA receiver(s) mounted on the surgical instrument.

Current solutions to this difficult include the use of manufacturing-time-intensive robotic mapping procedures to correct the tracking errors. However, such systems and methods must still be used so as to avoid positions and orientations of instruments, patient anatomies, and/or detectors that result in failure to track. Therefore, users of such systems and methods end up with a situation where (1) the detector cannot be tracked in some desired positions and orientations, (2) the receivers stick out from the detector so as to avoid interference and, in doing so, get in the way of medical or imaging procedures, and/or (3) an expensive mapping manufacturing process is necessary.

Another current area of application of current systems and methods is the use of a surgical microscope for surgery inside a skull. Here, the fluoroscope described above is typically replaced with a microscope.

In this application, an ISCA transmitter is rigidly fixed to the skull to provide the dynamic reference to the patient's anatomy. One or two ISCA receivers are attached to the surgical instrument to track the position and orientation of the instrument with respect to the ISCA transmitter, and thus with respect to the patient's anatomy. The real-time position and orientation of the instrument are superimposed on pre-operative images of the patient's anatomy, similar to as described above.

One or two ISCA receivers are mounted on the surgical microscope to permit tracking the microscope's line-of-sight with respect to the ISCA transmitter, and thus with respect to the patient's anatomy.

The position of the microscope's focal point along the microscope's line-of-sight can be read from the microscope. This information permits the position of the microscope's focal point to be determined with respect to the ISCA transmitter, and thus with respect to the patient's anatomy.

The real-time position and orientation of the microscope's focal point and focal axis can then be superimposed on pre-operative images of the patient's anatomy. The real-time position and orientation of the instrument can also be superimposed on pre-operative images of the patient's anatomy.

In general, the microscope contains a lot of electrically-conductive material which distorts the magnetic fields near the microscope, therefore leading to tracking errors. To avoid inaccurate tracking, the ISCA receivers must be then mounted spaced away from the microscope. The "spaced-away" receivers can get in the way of the surgeon's work. On the other hand, the microscope is far enough away from the ISCA transmitter and from the ISCA receivers mounted on the surgical instrument so that the microscope does not significantly distort the magnetic fields measured by the ISCA receivers mounted on the surgical instrument.

Thus, a need exists for a navigation system and method employing a tracking technology that reduces the amount of interference experienced by trackers so as to increase the accuracy and precision of such a system and method and to decrease the amount of space required for such a system and method. Single-coil EM trackers are significantly less susceptible to the field-distorting effects of nearby materials than are ISCA EM trackers. Therefore, by converting systems and methods such as fluoroscope and microscope applications from ISCA EM tracking to single-coil EM tracking can reduce the space required and the amount of interference.

However, in order to perform such a conversion, one would need to first convert the ISCA transmitter to an ISCA receiver, then mount a new array of transmitter coils close to the working volume but out of the way of the surgeon. In addition, one would need to add tracker electronics to drive the new array of transmitters, add tracker electronics to receive the signals from the new receiver, and modify the tracker software to track each ISCA receiver as a group of single coils and to calculate the position and orientation (all six degrees of freedom) of each ISCA receiver. Yet, the big disadvantage of such a conversion is the need to find a place to put the array of transmitter coils. To work well, this array needs to be physically spread out in space.

Another solution could be to employ a system and method that permits tracking of ISCA trackers and single-coil trackers one at a time. In such a system and method, a user of the system would need to continually switch back and forth between tracking the position and orientation of the ISCA trackers and the position and orientation of the single-coil trackers. This back and forth switching would not permit continuous tracking of both the ISCA trackers and single-coil trackers and would contribute additional complexity to the system and method. Therefore, a need exists for a system and method that can simultaneously track multiple coil architectures.

BRIEF SUMMARY OF THE INVENTION

The presently described technology provides a method for simultaneously employing two or more coil architectures in an electromagnetic ("EM") tracking system. The method includes providing an EM transmitter that includes three single-coil transmitters, one or more EM receivers each including three single-coil receivers, and an EM receiver array that includes a plurality of single-coil receivers; tracking one or more of the single-coil transmitters of the EM transmitter with respect to the receiver array; and tracking one or more of the EM receivers with respect to the EM transmitter.

The presently described technology also provides an electromagnetic ("EM") tracking system configured to employ two or more coil architectures simultaneously. The system includes an EM transmitter comprising three single-coil transmitters, one or more EM receivers each comprising three single-coil receivers, an EM receiver array comprising a plurality of single-coil receivers, and tracker electronics. The tracker electronics is configured to track one or more of the single-coil transmitters of the EM transmitter with respect to the receiver array. The tracker electronics is also configured to track one or more of the EM receivers with respect to the EM transmitter.

The presently described technology also provides a computer-readable storage medium including a set of instructions for a computer. The set of instructions includes an individual coil tracking routine and a group coil tracking routine. The individual coil tracking routine is configured to track one or more of an orientation and a position of each single-coil transmitter in an Industry Standard Coil Architecture ("ISCA") transmitter with respect to an array of single-coil receivers. The group coil tracking routine is configured to track one or more of an orientation and a position of the ISCA transmitter with respect to an ISCA receiver. The individual coil tracking routine and the group coil tracking routine are configured to track one or more of the single-coil transmitter orientation and the single-coil transmitter position simultaneously with one or more of the ISCA transmitter orientation and the ISCA transmitter position.

BRIEF DESCRIPTION OF SEVERAL VIEWS OF THE DRAWINGS

FIG. 3 illustrates a flowchart of a method for simultaneously employing two or more coil architectures in an EM tracking system in accordance with an embodiment of the presently described technology.

Figure 1:
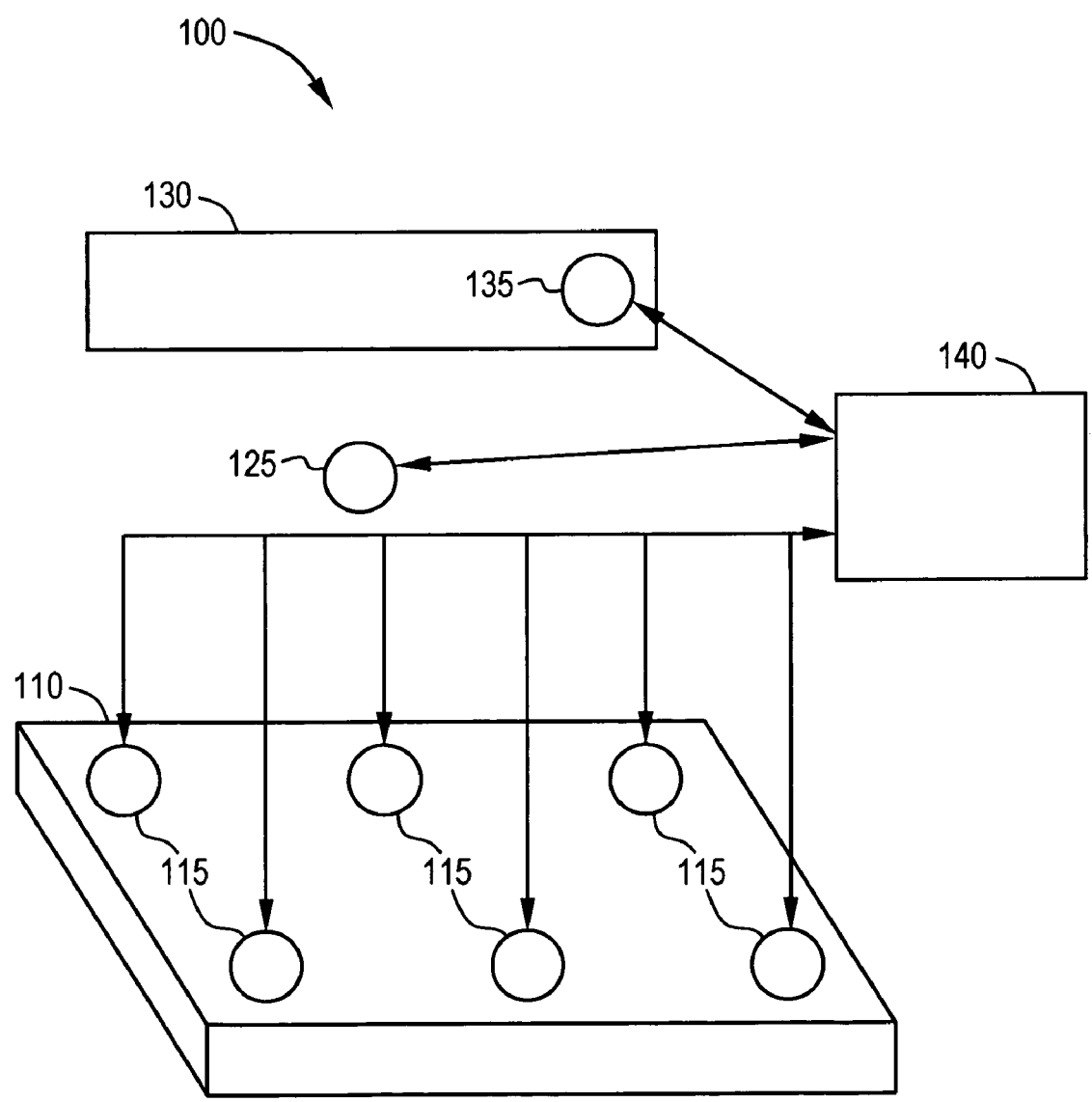
FIG. 1 illustrates an electromagnetic ("EM") tracking system used in accordance with an embodiment of the presently described technology.

The foregoing summary, as well as the following detailed description of certain embodiments of the presently described technology, will be better understood when read in conjunction with the appended drawings. For the purpose of illustrating the presently described technology, certain embodiments are shown in the drawings. It should be understood, however, that the presently described technology is not limited to the arrangements and instrumentality shown in the attached drawings.

DETAILED DESCRIPTION OF THE INVENTION

In accordance with an embodiment of the presently described technology, by combining ISCA and single-coil EM trackers into one integrated system, the system can gain the field-distortion immunity of the single-coil EM tracker where it is needed (on a fluoroscope X-ray detector and on the microscope, for example), while avoiding having to add a new array of transmitter coils where they are not desired.

FIG. 1 illustrates an electromagnetic ("EM") tracking system 100 used in accordance with an embodiment of the presently described technology. Tracking system 100 is configured to employ two or more coil architectures simultaneously. For example, tracking system 100 can be employed to track a position and/or orientation of one or more Industry Standard Coil Architecture ("ISCA") electromagnetic ("EM") trackers and a position and/or orientation of one or more single EM coils at the same time.

System 100 includes an array of single-coil receivers 115, an ISCA transmitter 125, an ISCA receiver 135, and tracker electronics 140. ISCA transmitter 125 can be mounted on a patient anatomy. For example, ISCA transmitter 125 can be rigidly attached to a skull or bone of a patient. In general, ISCA transmitter 125 can be rigidly mounted on a portion of a patient anatomy near the location or volume where a medical or surgical procedure is to be performed using system 100. ISCA transmitter 125 can serve as a dynamic reference for system 100. While a single ISCA transmitter 125 is shown in FIG. 1, any number of ISCA transmitters 125 can be used in accordance with various embodiments of the presently described technology. The illustration of a single ISCA transmitter 125 in FIG. 1 is not intended to limit the scope of any embodiment of the presently described technology.

In an embodiment, transmitter 125 can be a wireless transmitter. For example, transmitter 125 can be a wireless ISCA transmitter. In another embodiment, transmitter 125 can be a wired transmitter. Transmitter 125 can also be a sensor including additional electronics and capable of transmitting a signal through another object, such as a medical instrument or a combination of a medical instrument and a human body. For example, transmitter 125 can be a sensor employing a gyroscope or accelerometer.

ISCA receiver 135 can be mounted on an object 130 being navigated using system 100 such as a surgical instrument or implant. For example, receiver 135 can be attached to a tip of a reducing rod, a drill bit, debrider blade, or a guidewire. Similarly, receiver 135 can be attached to an artificial hip or knee implant. Receiver 135 can be added to an existing object 130 by wrapping a wire coil around a component of the device where tracking is desired to create an EM coil, for example. In order to reduce interference from the material of object 130, receiver 135 can be partially formed by wrapping a wire coil around object 130, thereby protecting the EM field from a source of interference.

Receiver 135 can be connected to the instrument or implant by embedding transmitting in the instrument or implant. For example, during the production of a reducing rod, drill bit, guidewire, artificial hip or artificial knee, pedicle screw, artificial disk, or the like, receiver 135 can be embedded into materials used to create the instrument or implant. By embedding receiver 135, it can be fixed in a given location within a device and therefore be resistant to movement independent of the device. However, other factors can require the embedding of receiver 135 into a medical device.

In an embodiment, receiver 135 can be a wireless receiver. A wireless receiver can draw power from an instrument on which receiver 135 is attached or embedded or can have a separate power source, for example. However, use of a battery as a power source may result in interference to system 100. In order to reduce this interference, receiver 135 can be partially formed by wrapping a wire coil around the power source, or battery, thereby protecting the EM field from the source of interference. Other sources of energy for receiver 135 may include induction or piezoelectric generation, for example.

In another embodiment, receiver 135 can be a wired receiver. While a single ISCA receiver 135 is shown in FIG. 1, any number of ISCA receivers 135 can be used in accordance with various embodiments of the presently described technology. The illustration of a single ISCA receiver 135 in FIG. 1 is not intended to limit the scope of any embodiment of the presently described technology.

The array of single-coil receivers 115 includes a plurality of single-coil EM receivers. The single-coil receivers 115 can be mounted on an imaging device 110 in system 100. Imaging device 110 can include any object used to image a portion of a patient anatomy. For example, imaging device 110 can include an x-ray detector or a surgical microscope.

In an embodiment, one or more single-coil receivers 115 in the array are single-coil dipole receivers. In another embodiment, one or more single-coil receivers 115 in the array are single-coil nearly-dipole receivers. In another embodiment, one or more single-coil receivers 115 in the array are single-coil non-dipole receivers. In another embodiment of the presently described technology, the array includes a combination of one or more single-coil dipole, nearly-dipole and/or non-dipole receivers.

In an embodiment, one or more single-coil receivers 115 can be wireless receivers. Wireless receivers can draw power from imaging device 110 on which receivers 115 are attached or embedded or can have a separate power source, for example. However, use of a battery as a power source may result in interference to system 100. In order to reduce this interference, receivers 115 can be partially formed by wrapping a wire coil around the power source, or battery, thereby protecting the EM field from the source of interference. Other sources of energy for receivers 115 can include induction or piezoelectric generation, for example.

In another embodiment, one or more receivers 115 can be wired receivers. Data can be communicated over a wired connection between one or more receivers 115 and tracker electronics 140. In another embodiment, power can be supplied to one or more receivers 115 via the wired connection.

In an embodiment, the array of single-coil receivers 115 includes six single-coil receivers. In another embodiment, the array can include a plurality of single-coil receivers 115 other than six receivers 115.

In an embodiment, one or more of the single-coil receivers 115 in the array are mounted on imaging device 110. For example, one or more of the single-coil receivers 115 in the array can be removably attached on imaging device 110.

In an embodiment, one or more of the single-coil receivers 115 in the array are integrated into imaging device 110. For example, during manufacture of imaging device 110, one or more single-coil receivers 115 can be inserted into the material forming a portion of imaging device 110.

The array of single-coil receivers 115 can be mounted or integrated in imaging device 110 in such a way so as to fit into the mechanical space available on or in device 110. For example, due to requirements of device 110, receivers 115 may only be able to be mounted or integrated into device 110 along an external perimeter of device 110. In an example of an x-ray detector as device 110, receivers 115 can be mounted on or integrated in the outer edge of the detector so as not to interfere with an imaging area in the center of the detector.

In an embodiment, the array of receivers 115 can include a printed circuit board. For example, a printed circuit board can be fabricated so as to include one or more single-coil receivers 115. The array of single-coil receivers 115 can then be formed by a printed circuit board that includes a plurality of single-coil receivers 115, a plurality of such printed circuit boards, and/or a combination of single-coil receivers 115 and printed circuit boards that include single-coil receivers 115.

In an embodiment, device 110 can be formed of electrically-conductive and/or ferromagnetic materials. Such materials can distort magnetic fields near device 110. However, the field of distortion caused by device 110 can be determined by methods known to those of skill in the art. Once this field is known, the field can be included in a model of magnetic fields and distortions within and/or affecting system 100. In such a scenario, the distortion field caused by device 110 can be incorporated into the model of system 100. Therefore, the distorting effects of device 110 may be reduced and/or eliminated from the tracking of one or more transmitters 125 with respect to the array of single-coil receivers 115.

In an embodiment, ISCA transmitter 125 can be replaced by an ISCA receiver attached to a patient anatomy, ISCA receiver 135 can be attached to an object 130 being navigated, and the array of single-coil receivers 115 can be replaced by an array of single-coil transmitters. In such an embodiment, one or more receivers 115 and/or ISCA receiver 135 are tracked with respect to ISCA transmitter.

In another embodiment, ISCA transmitter 125 can be replaced by an ISCA receiver attached to a patient anatomy, ISCA receiver 135 can be attached to an object 130 being navigated, and the array of single-coil receivers 115 can be replaced by an array of single-coil transmitters. If imaging device 110 is present, ISCA receiver 135 and the array of single-coil receivers 115 can be tracked with respect to ISCA receiver 125. If imaging device 110 is removed from the system, an additional transmitter can be added to the system so that ISCA receivers 125 and 135 can be tracked with respect to the additional transmitter.

Tracker electronics 140 includes any device capable of and/or configured to track a position and/or orientation of one or more ISCA receivers 135 with respect to one or more ISCA transmitters 125. In addition, tracker electronics 140 includes any device capable of and/or configured to track a position and/or orientation of one or more single-coil transmitters (such as the three single-coil transmitters that together form ISCA transmitter 125, for example) with respect to one or more of the single-coil receivers 115 in the array of single-coil receivers.

In an embodiment, a connection between ISCA transmitter 125 and tracker electronics 140 is a wired connection over which data is transmitted. In another embodiment, the connection between ISCA transmitter 125 and tracker electronics 140 is a wireless connection over which data is transmitted. In another embodiment, the connection between ISCA transmitter 125 and tracker electronics 140 is a wired connection over which only power is supplied to transmitter 125. In another embodiment, the wireless connection between ISCA transmitter 125 and tracker electronics 140 is a wireless connection over which only power is supplied to ISCA transmitter 125. In another embodiment, there is no connection between ISCA transmitter 125 and tracker electronics 140, and ISCA transmitter 125 is powered by one or more batteries.

In an embodiment, a connection between ISCA receiver 135 and tracker electronics 140 is a wired connection over which data is transmitted. In another embodiment, the connection between ISCA receiver 135 and tracker electronics 140 is a wireless connection over which data is transmitted.

In an embodiment, connections between each of the array of single-coil receivers 115 and tracker electronics 140 is a wired connection over which data is transmitted. In another embodiment, connections between each of the array of single-coil receivers 115 and tracker electronics 140 is a wireless connection over which data is transmitted.

In operation, ISCA transmitter 125 emits quasi-static magnetic fields. For example, each coil of transmitter 125 can emit a magnetic field. The coils of ISCA receiver 135 measure these fields. These field measurements are communicated from ISCA receiver 135 to tracker electronics 140. From these field measurements, the position and/or orientation of receiver 135 with respect to transmitter 125 is determined.

In another embodiment of the presently described technology, the field measurements are communicated to tracker electronics 140 and the position and/or orientation of transmitter 125 with respect to receiver 135 is determined.

In an embodiment of the presently described technology, one or more mathematical models of magnetic field interference(s) can also be used by tracker electronics 140 to determine the position and/or orientation of receiver 135 with respect to transmitter 125 or the position and/or orientation of transmitter 125 with respect to receiver 135. As described above, in an embodiment of the presently described technology, the mathematical model(s) can include a model of magnetic field interference(s) caused by imaging device 110.

In an embodiment of the presently described technology, tracker electronics 140 determines or tracks six degrees of freedom of transmitter 125 with respect to receiver 135. In another embodiment, tracker electronics 140 determines or tracks six degrees of freedom of receiver 135 with respect to transmitter 125. The six degrees of freedom includes three degrees of freedom of position and three degrees of freedom of orientation.

Tracker electronics 140 can also track the position and/or orientation of each coil of transmitter 125 independently with respect to the array of single-coil receivers 115. The three coils of transmitter 125 are used by tracker electronics 140 as three single single-coil transmitters in a three-channel single-coil tracker. As described above, existing tracker electronics can track the position and/or orientation of two or three single-coil transmitters (or receivers) simultaneously. If the two or more single coils are mounted rigidly with respect to each other and the axes of the coils point in different directions, the single coils can be tracked as two or more single coils. As such, all six degrees of freedom (three of position and three of orientation) can be tracked by tracker electronics for the set of single coils.

In a similar manner, tracker electronics 140 can track a position and/or orientation of each single-coil transmitter in ISCA transmitter 125 simultaneously. As the three transmitter coils of ISCA transmitter 125 are preferably mounted rigidly with respect to each other and as the axes of the transmitter coils preferably point in different directions, the single-coil transmitters can be tracked as three single transmitter coils. As such, all six degrees of freedom (three of position and three of orientation) of transmitter 125 with respect to the array of single-coil receivers 115 can be tracked by tracker electronics 140.

As described above, each coil of ISCA transmitter 125 can emit a quasi-static magnetic field. Receiver coils 115 of the array then measure these fields and communicate the measurements to tracker electronics 140. Based on these field measurements, the position and/or orientation of the single-coil receivers 115 with respect to transmitter 125 can be determined.

In another embodiment of the presently described technology, the field measurements are communicated to tracker electronics 140 and the position and/or orientation of transmitter 125 with respect to the array of single-coil receivers 115 is determined.

In an embodiment of the presently described technology, one or more mathematical models of magnetic field interference(s) can also be used by tracker electronics 140 to determine the position and/or orientation of the array of single-coil receivers 115 with respect to transmitter 125 or the position and/or orientation of transmitter 125 with respect to the array of single-coil receivers 115. As described above, in an embodiment of the presently described technology, the mathematical model(s) can include a model of magnetic field interference(s) caused by imaging device 110.

By tracking the position and/or orientation of ISCA transmitter 125 with respect to ISCA receiver 135 (as described above), system 100 can track the position and orientation of a surgical instrument 130 with respect to a patient anatomy to which ISCA transmitter 125 is mounted.

In an embodiment, tracker electronics 140 can include a large number of transmitter coil drivers (to accommodate a large number of transmitter coils used simultaneously, for example). Tracker electronics 140 can also include a modular design permitting additional transmitter coil drivers to be added based on a coil architecture in use. Wireless transmitters have no direct, physical connection with the system 100 and can be added to tracker electronics 140 with minimal effort.

Waveforms for transmitter coil drivers can be stored in a computer-readable memory, such as a random access memory (RAM) or hard disk drive, or can be generated on-the-fly by a software-controlled signal generator, such as a direct digital synthesizer (DDS), for example. Driver waveforms can be changed for different coil architectures by changing data in the RAM or other memory storing the waveforms or by adjusting settings of the software-controlled generator.

Driver waveforms can be distinguished using sine waves of different frequencies, for example. A similar effect can be accomplished by using waveforms that are nonzero at different times or by using a spread-spectrum code division technique.

Tracker electronics 140 can include a large number of receiver coil preamplifier channels (to accommodate a large number of receiver coils used simultaneously, for example). Alternatively, tracker electronics 140 can include a modular design allowing additional receiver coil drivers to be added based on a coil architecture(s) in use. Wireless receiver coil preamplifer channels can be added as well.

Signals emitted from receiver preamplifiers can be transmitted to analog-to-digital converters (ADCs). The ADCs can digitize the receiver preamplifier signals. Digital signals output from the ADCs are processed by one or more sets of instructions for a computer stored on a computer-readable storage medium. The set(s) of instructions can be embodied in one or more computer software applications, for example. In an embodiment, the software is stored in RAM or other memory. The software extracts desired frequency components of the digital signals. The frequency components can be further processed to calculate the position and orientation of the receiver assembly or assemblies, for example.

Since the software is stored in memory, algorithms, coil models, and processing schemes included in or generated by the software can be easily altered by modifying, reconfiguring, or replacing the software, for example. Software can be modified to accommodate various coil architectures or system parameters. In an embodiment, algorithms for multiple coil architectures can be loaded in memory. Multiple coil architecture algorithms and models, for example, allow multiple coil architectures to be run simultaneously. Rapid switching between architectures can also be facilitated using multiple configurations. In an embodiment, tracker electronics 140 can register multiple coordinate systems for multiple architectures.

In an embodiment, instead of requiring rapid switching between multiple and single coil architectures, the software running or operating on tracker electronics 140 can simultaneously track one or more positions and/or orientations of multiple and single coil transmitters and/or receivers simultaneously. In other words, in accordance with an embodiment of the presently described technology, tracker electronics 140 is not limited to tracking one type of coil architecture at a time. Instead, multiple coil architectures can be used in a single system 100 simultaneously to maximize the benefits realized by each coil architecture.

For example, tracker electronics 140 can track the multiple coils of an ISCA transmitter or receiver individually or as a group. In other words, tracker electronics 140 can track a position and orientation of each coil in ISCA transmitter 125 as an individual single-coil transmitter. As described above, typically five degrees of freedom (three of position and two of orientation) can be tracked for each single-coil tracker, as well as the gain of the single-coil tracker. However, as the axes of the three coils in ISCA transmitter 125 point in different directions, tracker electronics 140 is able to track six degrees of freedom of position and orientation of ISCA transmitter 125 with respect to the array of single-coil receivers 115. Moreover, tracker electronics 140 can simultaneously track ISCA transmitter 125 as an ISCA tracker and not as a grouping of three individual single-coil trackers.

Figure 2:
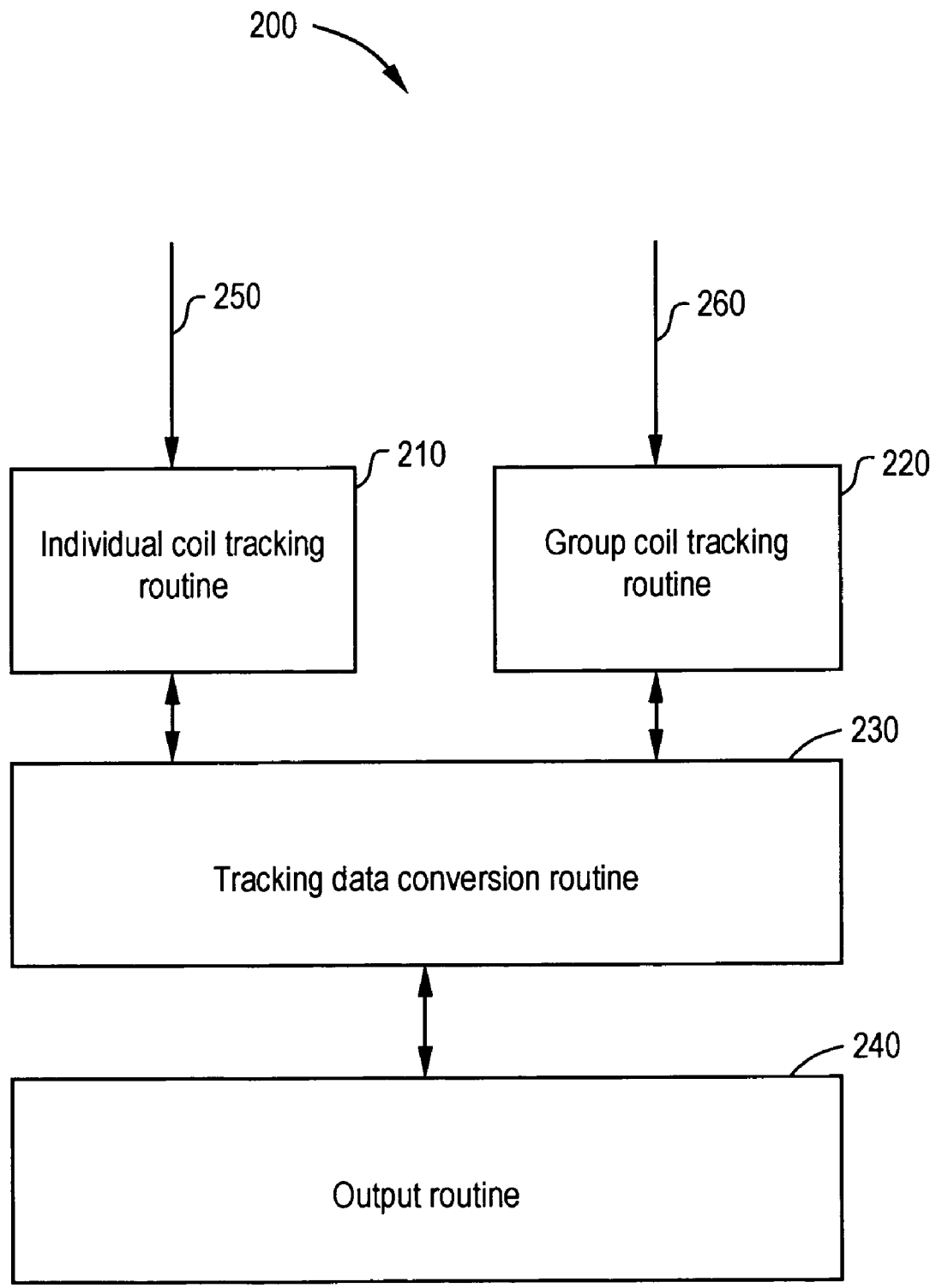
FIG. 2 illustrates a set of instructions for a computer that are stored on a computer-readable storage medium in tracker electronics in accordance with an embodiment of the presently described technology.

FIG. 2 illustrates a set of instructions 200 for a computer that are stored on a computer-readable storage medium in tracker electronics 140 in accordance with an embodiment of the presently described technology. Set of instructions 200 includes an individual coil tracking routine 210, a group coil tracking routine 220, a tracking data conversion routine 230, and a position and/or orientation output routine 240. The technical effect of set of instructions 200 is to permit the tracking of EM trackers using multiple coil architectures in a single EM tracking system.

Individual coil tracking routine 210 includes instructions for a computer that are configured to track a position and/or orientation of one or more single-coil transmitters with respect to one or more single-coil receivers and/or a position and/or orientation of one or more single-coil receivers with respect to one or more single-coil transmitters. For example, individual coil tracking routine 210 is configured to track a position and/or orientation of each coil in ISCA transmitter 125 individually with respect to the array of single-coil receivers 115.

Group coil tracking routine 220 includes instructions for a computer that are configured to track a position and/or orientation of one or more multiple coil transmitters with respect to one or more multiple coil receivers and/or a position and/or orientation of one or more multiple coil receivers with respect to one or more multiple coil transmitters. For example, group coil tracking routine 220 is configured to track a position and/or orientation of ISCA transmitter 125 (as a group of coils) with respect to one or more ISCA receivers 135.

In an embodiment of the presently described technology, an ISCA architecture and a single coil architecture can be running simultaneously in system 100. For example, as described above, ISCA transmitter 125 can be mounted on a patient anatomy, ISCA receiver 135 can be mounted on instrument 130, and the array of single-coil receivers 115 can be mounted on imaging device 110.

As described above, one or more individual coils of ISCA transmitter 125 can emit a quasi-static magnetic field. Receiver coils 115 of the array then measure one or more of these fields and communicate the measurements to tracker electronics 140. Individual coil tracking routine 210 can receive these measurements and communicate them to tracking data conversion routine 230. Tracking data conversion routine 230 is a set of instructions for a computer that is configured to convert the field measurements into a position and/or orientation of one or more of the individual coils of ISCA transmitter 125 with respect to the array of single-coil receivers 115 (and vice-versa). Tracking data conversion routine 230 can then communicate the position and/or orientation of one or more of the coils in ISCA transmitter 125 to output routine 240. Output routine 240 is a set of instructions for a computer that is configured to communicate the position and/or orientation of one or more of the coils in ISCA transmitter 125 to an output device. The output device can include any device capable of displaying such information, such as a computer monitor or display.

Also as described above, ISCA transmitter 125 emits quasi-static magnetic fields. For example, each coil of transmitter 125 can emit a magnetic field. The coils of ISCA receiver 135 can measure these fields. These field measurements can be communicated from ISCA receiver 135 to group coil tracking routine 220 of tracker electronics 140. Group coil tracking routine 220 can receive these measurements and communicate them to tracking data conversion routine 230. Tracking data conversion routine 230 is a set of instructions for a computer that is also configured to convert the field measurements into a position and/or orientation of ISCA transmitter 125 with respect to ISCA receiver 135 (and vice-versa). Tracking data conversion routine 230 can then communicate the position and/or orientation of one or more of the coils in ISCA transmitter 125 to output routine 240. Output routine 240 is a set of instructions for a computer that is configured to communicate the position and/or orientation of ISCA transmitter 125 to an output device. The output device can include any device capable of displaying such information, such as a computer monitor or display.

For each of the above examples, while a position and/or orientation of one or more transmitter coils (individually or as a group) can be determined with respect to one or more receiver coils (individually or as a group), as appreciated by one or ordinary skill in the art, one or more positions and/or orientations of receiver coil(s) (individually or as a group) can also be determined with respect to transmitter coil(s) (individually or as a group).

Additionally, the array of single-coil receivers 115 can be used to track a position and/or orientation of ISCA transmitter 125. The array of single-coil receivers 115 can be used to determine position and orientation information (including roll, for example) of ISCA transmitter 125 with respect to the array of single-coil receivers 115. Then, the position and orientation of ISCA receiver 135 with respect to the array of single-coil receivers 115 can be determined.

In an embodiment of the presently described technology, if system 100 is employed with an x-ray imaging device, such as a fluoroscope, system 100 can then be employed to calculate and display or superimpose a real-time position and orientation of the surgical instrument 130 on one or more stored fluoroscopic images of a patient anatomy.

In another embodiment of the presently described technology, if system 100 is employed with a surgical microscope, a real-time position and orientation of the surgical instrument (the surgical microscope) 130 can be displayed or superimposed on one or more pre-operative images of the patient anatomy.

In addition and in an embodiment of the presently described technology, by tracking the position and orientation of one or more ISCA receivers 135 mounted on surgical instrument (the surgical microscope) 130, system 100 can be employed to track the line-of-sight of the surgical microscope with respect to ISCA transmitter 125, and therefore with respect to the patient's anatomy.

In addition and in an embodiment of the presently described technology, the position of the surgical microscope's focal point along the surgical microscope's line-of-sight can be read from the surgical microscope. In other words, the surgical microscope can communicate the position of its focal point along its line-of-sight to a user of system 100 and/or tracker electronics 140. This focal point position can then be employed by tracker electronics 140 (if directly communicated to tracker electronics 140 or if input to tracker electronics 140 by a user of system 100) to determine the position of the surgical microscope's focal point with respect to ISCA transmitter 125, and therefore with respect to the patient's anatomy.

The real-time position and orientation of the surgical microscope's focal point and/or the focal axis of the microscope can then be superimposed on one or more pre-operative images of the patient anatomy. In an embodiment, the real-time position and orientation of surgical instrument 130 can also be superimposed on one or more pre-operative images of the patient's anatomy.

FIG. 3 illustrates a flowchart of a method 300 for simultaneously employing two or more coil architectures in an EM tracking system in accordance with an embodiment of the presently described technology. First, at step 310, an ISCA transmitter 125 is mounted on a patient anatomy, as described above. Next, at step 320, one or more ISCA receivers 135 are mounted on a surgical instrument 130, as described above.

Next, at step 330, an array of single-coil receivers 115 is mounted on an imaging device 110, also as described above.

Next, at step 340, a position and/or orientation of one or more of the individual coils in ISCA transmitter 125 is tracked relative to the array of single-coil receivers 115, as described above. Simultaneous with step 340, at step 350, a position and/or orientation of one or more ISCA receivers 135 is tracked with respect to ISCA transmitter 125, also as described above.

In an embodiment, any one or more of steps 310, 320, and 330 can be performed in any other order. For example, method 300 can proceed in order of steps 320, 330, 310 or 330, 310, 320, or 310, 330, 320 or 320, 310, 330 or 330, 320, 310. In another embodiment, any one or more of steps 310, 320, and 330 can be performed simultaneously.

While particular elements, embodiments and applications of the presently described technology have been shown and described, it is understood that the presently described technology is not limited thereto since modifications may be made by those skilled in the art, particularly in light of the foregoing teaching. For example, one of ordinary skill in the presently described technology will appreciate that while the operation of the above system and method may be described as tracking a transmitter with respect to a receiver, the same system and method may also track a receiver with respect to a transmitter. It is therefore contemplated by the appended claims to cover such modifications and incorporate those features that come within the spirit and scope of the presently described technology.

What is claimed is:

1. A method for simultaneously employing two or more different coil architectures in an electromagnetic ("EM") tracking system, said method including:
   providing an EM transmitter, one or more EM receivers, and an EM receiver array, said EM transmitter comprising three single-coil transmitters and each of said EM receivers comprising three single-coil receivers, said receiver array comprising a plurality of single-coil receivers;
   tracking one or more of said single-coil transmitters of said EM transmitter with respect to said receiver array; and
   tracking one or more of said EM receivers with respect to said EM transmitter, wherein said step of tracking one or more of said single-coil transmitters of said EM transmitter with respect to said receiver array and said step of tracking one or more of said EM receivers with respect to said EM transmitter occur simultaneously.

2. The method of claim 1, wherein said EM transmitter is configured to be mounted on a patient anatomy.

3. The method of claim 1, wherein said EM receiver array is configured to be mounted on one or more of an x-ray detector and a surgical microscope.

4. The method of claim 1, wherein at least one of said EM receivers is configured to be mounted on a surgical instrument.

5. The method of claim 1, wherein one or more of said EM transmitter and said EM receivers is an Industry Standard Coil Architecture ("ISCA") combination of three coils.

6. The method of claim 1, wherein said receiver array includes at least six single-coil receivers.

7. The method of claim 1, wherein said receiver array includes one or more dipole, nearly-dipole, and non-dipole coils.

8. The method of claim 1, wherein said step of tracking one or more of said single-coil transmitters of said EM transmitter with respect to said receiver array includes tracking each of said single-coil transmitters as an individual single-coil transmitter.

9. An electromagnetic ("EM") tracking system configured to employ two or more different coil architectures simultaneously, said system including:
- an EM transmitter comprising three single-coil transmitters;
- one or more EM receivers each comprising three single-coil receivers;
- an EM receiver array comprising a plurality of single-coil receivers; and
- tracker electronics configured to track one or more of said single-coil transmitters of said EM transmitter with respect to said receiver array and to track one or more of said EM receivers with respect to said EM transmitter, wherein said tracker electronics is configured to simultaneously track one or more of said single-coil transmitters of said EM transmitter with respect to said receiver array and to track one or more of said EM receivers with respect to said EM transmitter.

10. The system of claim 9, wherein said EM transmitter is configured to be mounted on a patient anatomy.

11. The system of claim 9, wherein said EM receiver array is configured to be mounted on one or more of an x-ray detector and a surgical microscope.

12. The system of claim 9, wherein at least one of said EM receivers is configured to be mounted on a surgical instrument.

13. The system of claim 9, wherein one or more of said EM transmitter and said EM receivers is an Industry Standard Coil Architecture ("ISCA") combination of three coils.

14. The system of claim 9, wherein said receiver array includes at least six single-coil receivers.

15. The system of claim 9, wherein said receiver array includes one or more dipole, nearly-dipole, and non-dipole coils.

16. The system of claim 9, wherein said tracker electronics is configured to track each said single-coil transmitters as an individual single-coil transmitter.

17. A computer-readable storage medium including a set of instructions for a computer, said instructions including:
- an individual coil tracking routine configured to track one or more of an orientation and a position of each single-coil transmitter in an Industry Standard Coil Architecture ("ISCA") transmitter with respect to an array of single-coil receivers;
- a group coil tracking routine configured to track one or more of an orientation and a position of said ISCA transmitter with respect to an ISCA receiver,
- wherein said individual coil tracking routine and said group coil tracking routine are configured to track one or more of said single-coil transmitter orientation and said single-coil transmitter position simultaneously with one or more of said ISCA transmitter orientation and said ISCA transmitter position.

18. The set of instructions of claim 17, wherein said array includes at least six single-coil receivers.

19. The set of instructions of claim 17, wherein said array includes one or more dipole, nearly-dipole, and non-dipole receiver coils.

* * * * *